(12) United States Patent
Jitpraphai et al.

(10) Patent No.: US 8,263,097 B2
(45) Date of Patent: *Sep. 11, 2012

(54) METHODS AND COMPOSITIONS FOR TREATING ACNE

(75) Inventors: Waranush Jitpraphai, Scottsdale, AZ (US); Eugene Gans, Scottsdale, AZ (US)

(73) Assignee: Medicis Pharmaceutical Corporation, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/335,151

(22) Filed: Dec. 22, 2011

(65) Prior Publication Data

US 2012/0082710 A1   Apr. 5, 2012

Related U.S. Application Data

(63) Continuation of application No. 12/716,130, filed on Mar. 2, 2010.

(60) Provisional application No. 61/306,808, filed on Feb. 22, 2010, provisional application No. 61/157,817, filed on Mar. 5, 2009.

(51) Int. Cl.
*A61K 31/327* (2006.01)
*A61K 9/00* (2006.01)
*A61K 31/63* (2006.01)
*A61K 7/00* (2006.01)
*A61K 7/48* (2006.01)
*A61K 7/50* (2006.01)
*A61L 15/16* (2006.01)

(52) U.S. Cl. ..... 424/402; 424/446; 424/401; 424/78.03; 424/59; 514/714; 514/155; 510/475; 510/119; 510/120; 510/121

(58) Field of Classification Search .................. None
See application file for complete search history.

(56) References Cited

U.S. PATENT DOCUMENTS

| | | |
|---|---|---|
| 4,758,467 A | 7/1988 | Lempriere |
| 4,960,772 A | 10/1990 | Sebag et al. |
| 5,879,693 A | 3/1999 | Wolfe |
| 5,951,991 A | 9/1999 | Wagner et al. |
| 6,153,208 A | 11/2000 | McAtee et al. |
| 6,190,678 B1 | 2/2001 | Hasenoehrl et al. |
| 6,294,186 B1 | 9/2001 | Beerse et al. |
| 6,524,594 B1 * | 2/2003 | Santora et al. ............. 424/401 |
| 6,784,145 B2 | 8/2004 | Delambre et al. |
| 7,776,355 B2 | 8/2010 | Patel et al. |
| 2003/0194425 A1 | 10/2003 | Simon et al. |
| 2004/0147189 A1 | 7/2004 | Smith, III et al. |
| 2004/0167046 A1 | 8/2004 | Lukenbach et al. |
| 2004/0170670 A1 | 9/2004 | Smith et al. |
| 2004/0191300 A1 | 9/2004 | Von Der Fecht et al. |
| 2005/0025817 A1 | 2/2005 | Bhatia et al. |
| 2006/0051384 A1 | 3/2006 | Scholz et al. |
| 2006/0172904 A1 | 8/2006 | Bonafos |
| 2006/0177505 A1 | 8/2006 | Calduk |
| 2007/0099813 A1 | 5/2007 | Luizzi et al. |
| 2007/0269537 A1 | 11/2007 | Gupta |
| 2008/0026039 A1 | 1/2008 | Popp |
| 2009/0017147 A1 | 1/2009 | Lintner et al. |
| 2009/0018200 A1 | 1/2009 | Willemin et al. |
| 2009/0311308 A1 | 12/2009 | Strodtholz et al. |
| 2011/0262645 A1 | 10/2011 | Batchvarova et al. |

FOREIGN PATENT DOCUMENTS

| | | |
|---|---|---|
| DE | 10301839 A1 | 7/2004 |
| DE | 10301841 A1 | 7/2004 |
| EP | 1352950 A2 | 10/2003 |
| EP | 1779834 A2 | 5/2007 |
| GB | 2163947 A | 3/1986 |
| WO | 9531189 A1 | 11/1995 |
| WO | 9912519 A1 | 3/1999 |
| WO | 9913861 A1 | 3/1999 |
| WO | 2009137100 A2 | 11/2009 |

* cited by examiner

*Primary Examiner* — Brian-Yong S Kwon
*Assistant Examiner* — Hong Yu
(74) *Attorney, Agent, or Firm* — Reed Smith LLP; William J. McNichol, Jr.; Maryellen Feehery Hank

(57) ABSTRACT

A method for treating acne on the skin. The method has the steps of (a) providing an drapeable or flexible porous article impregnated with an aqueous cleansing composition having a carrier, benzoyl peroxide, and one or more cleansing agents; (b) contacting an area of the skin affected by acne with the porous article such that the skin is contacted by the composition; and (c) removing the composition from the skin wherein residual benzoyl peroxide remains on the skin in an anti-acne effective amount. There are also anti-acne compositions.

12 Claims, No Drawings

METHODS AND COMPOSITIONS FOR TREATING ACNE

CROSS-REFERENCE TO A RELATED APPLICATION

This application is a continuation of U.S. utility application Ser. No. 12/716,130 filed Mar. 2, 2010, which claims priority from provisional application No. 61/306,808, filed Feb. 22, 2010, and U.S. provisional application No. 61/157,817, filed Mar. 5, 2009, the entire contents of both applications which are incorporated herein by reference, including any references cited therein.

BACKGROUND OF THE INVENTION

1. Field of the Invention

The present invention relates to methods and compositions for preventing and/or treating acne on the skin.

2. Description of the Related Art

Acne is a condition of the human skin characterized by an excess flow of sebum, or skin oil, from the sebaceous glands located in the pilosebaceous apparatus. Sebum reaches the skin surface through the duct of the hair follicle. The presence of excessive amounts of sebum and slouched follicle cells in the duct and on the skin acts to block or stagnate the continuous flow of sebum from the follicular duct, thus producing a thickening and a solidification of the sebum to form a solid plug known as a comedone. When this process occurs, hyperkeratinization of the follicular opening is stimulated, thus tending to partially or completely close the duct. The usual results are papules, pustules, or cysts, often contaminated with bacteria which cause secondary infections and inflammation. Acne is particularly characterized by the presence of comedones, inflammatory papules, pustules, or cysts. The effect of acne ranges from slight to substantial skin irritation and pitting to disfiguring scars.

Many topical therapeutic agents are employed in the treatment of acne and seborrhea to prevent the blocking of the follicular duct, to reopen the duct once it has become blocked, to act against the infecting bacteria or the thickened sebum and resulting inflammation, or to provide combinations of each of these actions. The horny outer layer of the skin, which is known as the stratum corneum, is formed of dead cells composed largely of keratin. Therapeutic agents which act to prevent the blocking of the follicular duct by promoting the removal or sloughing off of excess keratin are known as keratolytic agents.

Benzoyl peroxide has been used as a very effective keratolytic and antibacterial agent in the treatment of acne. The topical application of benzoyl peroxide for skin lesion therapy is well known. For example, U.S. Pat. Nos. 5,445,823; 5,545,407; 5,648,389; and 5,932,228 disclose compositions for treating acne and other skin lesions and also to methods of treatment utilizing these compositions. These compositions and methods of treatment employ benzoyl peroxide plus compounds for reducing the skin irritation associated with benzoyl peroxide, and a topical carrier.

One form for advantageously administering anti-acne agents is application to the skin via impregnated small cloth towelettes, wipes, or applicator porous articles. The cloths can be packaged in plural in a sealed pouch or individually. Examples of such cloths are disclosed in U.S. Pat. Nos. 5,242,433; 5,254,109; 5,368,581; 5,417,674; 5,460,620; 5,470,323; 5,538,732; 5,562,642; 6,001,380; and 6,740,330 as well as U.S. Published Patent Application Publication Nos. 2005/0025817, 2005/0100585, and 2005/0232978.

SUMMARY OF THE INVENTION

The invention described herein provides new methods for treating and/or preventing acne and new compositions useful in such respects.

In one aspect, the invention provides new methods for treating acne with benzoyl peroxide that improve user compliance and/or contact of the benzoyl peroxide with the skin. According to the present invention, there is, in a particular exemplary aspect, provided a method for treating acne on the skin, comprising: (a) providing an drapeable or flexible porous article impregnated with an aqueous cleansing composition comprising a carrier, benzoyl peroxide, and one or more cleansing agents; (b) contacting an area of the skin affected by acne with the porous article such that the skin is contacted by the composition; and (c) removing the composition from the skin wherein residual benzoyl peroxide remains on the skin in an anti-acne effective amount, preferably while surface dirt and/or irritants are removed.

Further according to the present invention, there is provided an exemplary anti-acne composition. The composition has water, benzoyl peroxide, a salt of a fatty acid ester having from 12 to 20 carbon atoms, and a salt of a fatty acid isethionate having from 12 to 20 carbon atoms. The fatty acid ester salt and the fatty acid isethionate salt are present in an amount sufficient to render the composition foamable and to maintain a substantially homogeneous dispersion of the benzoyl peroxide in the composition to cleanse and medicate the skin.

Still further according to the present invention, anti-acne compositions are provided. In one aspect, the composition comprises water, benzoyl peroxide, a cellulose ether, and a polyacrylic polymer. The cellulose ether and the polyacrylic polymer are present in an amount sufficient to impart substantial stability to the composition (e.g., in terms of reduced phase separation). The cellulose ether and the polyacrylic polymer also keep the benzoyl peroxide uniformly suspended within the impregnated cloth and minimize preferential binding to the cloth (and/or erratic or uneven binding to the skin) and enhance contact with and/or bioavailability to the skin.

DETAILED DESCRIPTION OF THE INVENTION

Anti-acne compositions of the invention typically are impregnated in an absorbent porous article. Impregnation refers to the entrainment of the composition in the porous article and is deemed to include both absorption and adsorption. The active agent, benzoyl peroxide, is released from the porous article when the composition is transferred from the porous article to a user's skin. Depending on conditions of use, any useful portion or substantially all of the benzoyl peroxide may be released.

As used herein, the term "acne" means a common inflammatory disease of the pilosebaceous glands characterized by comedones, erythema, general irritation, papules, pustules, inflamed nodules, superficial or greater pus-filled cysts, and (in extreme cases) canalizing and deep, inflamed, sometimes purulent sacs. Types of acne within the scope of the present subject matter include acne vulgaris or topical acne. As described above, "acne" is believed to be caused by an interaction among hormones, keratin, sebum, and bacteria. One common bacterial causative agent is Propionibacterium acnes.

Benzoyl peroxide is used in the composition an anti-acne agent. Benzoyl peroxide has antimicrobial and antibacterial effect as well as a keratolyic and drying effect. Benzoyl peroxide is present in the composition at up to wt %, preferably from about 1 wt % to about 15 wt %, and most preferably from about 3 wt % to about 9 wt % based on the total weight of the composition.

The composition has a surfactant system of one or more surfactants. Benzoyl peroxide is relatively insoluble in water, so it can be desirable to form a suspension of the benzoyl peroxide in aqueous media in the impregnant composition and for the purpose of stabilization and entrainment therein. Further, the surfactant system is selected to provide for release of the benzoyl peroxide from the porous article upon contact with the skin and retention of a residue or portion of the benzoyl peroxide after the composition has been rinsed or otherwise substantially removed from the skin.

The surfactant system (one or more surfactants) is present in the impregnant composition in an amount of about 0.1 wt % to about 75 wt % of the total composition. Preferably, the surfactant system is present from about 4 wt % to about 40 wt % of the total composition. More preferably, the surfactant system is present from about 10 wt % to about 30 wt % of the total composition.

The surfactant system may have surfactants known in the art, such as anionic, nonionic, amphoteric, cationic, and zwitterionic surfactants. Preferred systems have one or more anionic surfactants for the cleansing and lathering effects.

The surfactant system preferably has one or more anionic surfactants present in an amount of about 0.1 wt % to about 75 wt % and more preferably about 4 wt % to about 40 wt % based on the total weight of surfactants in the surfactant system.

Examples of useful anionic surfactants include carboxylates, amino acid derivatives, alkyl sulphates, alkyl ether sulfates, sulphonates, isethionates, taurates, sulfosuccinates, alkyl sulfoacetates, phosphates, alkyl phosphates, lauramine oxide, and any combination thereof. Preferred anionic surfactants include salts of fatty acid esters having from 12 to 20 carbon atoms, such as sodium methyl cocoyl taurate; salts of fatty acid isethionates having from 12 to 20 carbon atoms, such as sodium cocoyl isethionate; salts of fatty acid sulfoacetates having from 12 to 20 carbons, such as sodium lauryl sulfoacetate; and disalts of fatty acid sulfosuccinates having from 12 to 20 carbons, such as disodium laureth sulfosuccinate.

In preferred compositions, salts of fatty acid esters having from 12 to 20 carbon atoms and salts of fatty acid isethionates having from 12 to 20 carbons are together present at a total of about 8 to about 30 wt %, such as about 8 to about 20 wt % active material (e.g., sodium cocoyl isethionate), typically about 9 to about wt % active material (e.g., about 10 to about 12% active material), but alternatively about 12 to about 27 wt % based on the total weight of the composition. In one aspect, the salt is sodium methyl cocoyl taurate. In this and other aspects, a relatively lower concentration can be suitable (e.g., about 1 to about wt %, such as about 2 to 10 about 8 wt % active material).

In more preferred compositions, salts of fatty acid sulfoacetates having from 12 to 20 carbons and disalts of fatty acid sulfosuccinates having from 12 to 20 carbons are together present at a total of about 1 to about 10 wt %, more preferably at a total of about 2 to about 8 wt %, and most preferably at a total of about 3 to about 6 wt % based on the total weight of the composition.

Examples of useful nonionic surfactants include alkanolamides, amine oxides, esterified carboxylic acids, ethoxylated alcohols, poloxamers, and any combination thereof.

Examples of useful amphoteric/zwitterionic surfactants include betaine surfactants, such as cocamidopropyl betaine and lauramidopropyl betaine.

Examples of useful cationic surfactants include alkylamines, alkylimidazolines, and quaternary ammonium compounds. Examples of cationic surfactants include, benzethonium chloride, cetrimide, cetylpyridinium chloride, stearalkonium chloride and dicetyldimonium choride.

The impregnant composition can be aqueous or nonaqueous or aqueous/nonaqueous, i.e., an emulsion. In an aqueous composition, water can be present as a carrier or solvent for suspending, dispersing, and/or dissolving composition ingredients. In an aqueous composition, the water is present in the composition at up to 90 wt %, preferably about 10 wt % to about 90 wt %, and more preferably from about 20 wt % to about 80 wt %, and most preferably from about 40 wt % to about 80 wt % based on the total weight of the composition. Useful nonaqueous and/or hydrophilic solvents include monohydric alcohols, polyhydric alcohols, and C12_alkyl benzoates and can be present in the composition in the percentages indicated above for water.

Selection of viscosity is important to the storage stability of the liquid impregnant composition and the rheology or flow properties of the composition during impregnation of the porous article. Viscosity may also vary depending on the form of the composition employed, e.g., gel, dispersion, emulsion, or suspension. The gel form is preferred. Viscosity of the composition is preferably from about 500 cP to about 3,000,000 cP, more preferably about 30,000 cP to about 150,000 cP, and most preferably about 35,000 cP to about 65,000 cP.

The viscosity of the composition can be regulated with the presence of one or more gelling agents and/or a thickening agents as optional ingredient(s). The gelling agent(s) and/or thickening agents are present in the composition at up to 30 wt %, preferably from about 0.1 wt % to about 10 wt % based on the total weight of the composition.

Examples of useful gelling agents include various cellulose agents, including cellulose ethers such as carboxymethylcellulose sodium, carboxymethylcellulose calcium, hydroxypropyl cellulose, hydroxyethylmethyl cellulose, ethylcellulose, hydroxyethylcellulose, methylcellulose, hydroxypropylcellulose, and hydroxypropylmethylcellulose. A preferred cellulose ether is hydroxypropylmethylcellulose. Other useful cellulose agents include cellulose gum, xanthan gum, gum arabic, gum tragacanth, locust bean gum, guar gum, derivatives thereof, and any combination thereof. The gelling agent(s) (and other possible components of the composition) preferably do not stain or otherwise impair hair, skin, and/or clothing.

When one or more cellulose ethers are present, it is preferably present from about 0.1 wt % to about 3 wt % and more preferably from about 0.45 wt % to about 1 wt % in the composition.

Other useful gelling agents useful include polyacrylic polymers, carboxy vinyl polymers such as carboxypolymethylene, derivatives thereof, and any combination thereof. A preferred polyacrylic polymer is the carbomers, such as the Carbopol polymers available from Noveon Inc. A preferred polyacrylic polymer is an acrylates/Cio-3o alkyl acrylate crosspolymer.

Preferred polyacrylic polymers are carbomers. Examples of suitable carbomers are Carbopol 1342, Carbopol 940, Carbopol 941, Carbopol 980, Carbopol 981, Carbopol 1382, Carbopol 971P, Carbopol 974P, Carbopol 71G, Carbopol 910, Carbopol 934, Carbopol 934P, Carbopol 5984, Carbopol ETD, Carbopol Ultrez 10, Carbopol Ultrez 21, Pemulen TR-1, Pemulen TR-2, and any combination of the foregoing. Carbopol 1342 is a preferred carbomer.

When one or more polyacrylic polymers are present, it is preferably present from about 0.1 wt % to about 3 wt % and more preferably from about 0.45 wt % to about 1 wt % in the composition.

Examples of useful thickening agents include fatty alcohols of 10 to 24 carbon atoms, such as cetyl alcohol, cetearyl alcohol, cetostearyl alcohol, stearyl alcohol, lauryl alcohol, myristyl alcohol, arachidyl alcohol, behenyl alcohol, oleyl alcohol, and erucyl alcohol; fatty acids of 10 to 24 carbon atoms, such as stearic acid, myristic acid, lauric acid, arachidic acid, behenic acid, oleic acid, and erucic acid; fatty esters of 10 to 24 carbon atoms, such as sodium stearate, glyceryl monostearate and glyceryl monooleate; magnesium aluminum silicate; xanthan gum; PEG-150 pentaerythrityl tetrastearate; derivatives thereof; and any combination thereof. Preferred thickening agents are fatty alcohols, fatty acids, and fatty esters. More preferred thickening agents are fatty alcohols. A most preferred thickening agent is cetyl alcohol.

When one or more fatty alcohols, fatty acids, or fatty esters of 10 to 24 carbon atoms are present in the composition, it is preferably present from about 0.5 wt % to about 10 wt % and more preferably from about 0.5 wt % to about 3 wt %.

The thickening agent may also take the form of one or more organic waxes, such as emulsifying wax (nonionic emulsifying wax), anionic emulsifying wax, cetyl ester wax, microcrystalline wax, white wax, yellow wax, paraffin, synthetic waxes such as high molecular weight organic esters, and any combination of the foregoing.

The thickening agent may also take the form of one or more of the following: chitosan, carrageenan, colloidal silicon dioxide, hydroxypropyl starch, kaolin, polycarbophil, propylene glycol alginate, sodium alginate, alginic acid, tragacanth, acacia, trehalose, and any combination of the foregoing.

Preferred compositions further have a moisturizer. In some instances, benzoyl peroxide can dry out areas of the body to which compositions having it are applied. In these instances, it is desirable to include a moisturizer in the composition to help the body retain moisture to offset the drying effect of the benzoyl peroxide. Examples of useful moisturizers include glycerin, pentylene glycol, butylene glycol, polyethylene glycol, sodium pyrrolidone carboxylate, alpha-hydroxy acids, beta-hydroxy acids, polyhydric alcohols, ethoxylated and propoxylated polyols, polyols, polysaccharides, panthenol, pantethine, hexylene glycol, propylene glycol, polypropylene glycol, octyldodecanol, dipropylene glycol, sorbitol, sodium hyaluronate, sodium pyrrolidone carboxylic acid (sodium PCA), derivatives thereof, and any combination thereof. Preferred moisturizers are glycerin, sodium hyaluronate, and sodium PCA.

The composition may optionally further have a humectant. Examples of useful humectants include sorbitol, glycerin, sorbitol syrup, E965 maltitol, maltitol, maltitol syrup, E1200 polydextrose, E1518 glyceryl triacetate, triacetin, glyceryl triacetate, 1,2,3-propanetriyl triacetate, 1,2,3-propanetriol triacetate, triacetylglycerol, E1520 propylene glycol, 1,2-propanediol, 1,2-dihydroxypropane, methylethylene glycol, propane-1,2-diol, E420 sorbitol, propylene glycol, polyethylene glycol (PEG) esters, PEG-20 stearate, PEG-40 stearate, PEG-150 stearate, PEG-150 distearate, PEG-100 stearate, laureth-12, ceteareth-20, laureth-23, glycereth-7, glycereth-12, glycereth-26, PEG-4, PEG-6, PEG-8, PEG-12, PEG-32, PEG-75, PEG-150, derivatives thereof, and any combination thereof.

The composition optionally further has a pH modifier. Examples of useful pH modifiers include inorganic hydroxides, inorganic oxides, inorganic salts of weak acids, inorganic acids, organic acids, inorganic oxides, derivatives thereof, and any combination thereof. Examples of useful inorganic hydroxides include ammonium hydroxide, alkali metal hydroxide, alkaline earth metal hydroxides. Sodium hydroxide is a preferred pH modifier.

Examples of useful inorganic oxides include magnesium oxide, calcium oxide, derivatives thereof, and any combination thereof.

Examples of useful inorganic salts of weak acids useful herein include ammonium phosphate (dibasic), alkali metal salts of weak acids such as sodium acetate, sodium borate, sodium metaborate, sodium carbonate, sodium bicarbonate, sodium phosphate (tribasic), sodium phosphate (dibasic), potassium carbonate, potassium bicarbonate, potassium citrate, potassium acetate, potassium phosphate (dibasic), potassium phosphate (tribasic), alkaline earth metal salts of weak acids such as magnesium phosphate and calcium phosphate, derivatives thereof, and any combination thereof.

Examples of useful inorganic acids include hydrochloric acid, hydrofluoric acid, hydrobromic acid, nitric acid, nitrous acid, hydrocyanic acid, perchloric acid, chlorous acid, sulfurous acid, hypochlorous acid, phosphoric acid, acetic acid, sulfuric acid, derivatives thereof, and any combination thereof.

Examples of useful organic acids include lactic acid, citric acid, glutamic acid, methanoic acid, ethanoic acid, maleic acid and salts, glycolic acid and salts, benzoic acid, phenol, monochloroethanoic acid, dichloroethanoic acid, trichloroethanoic acid, butanoic acid, salicylic acid, glycolic acid, salts thereof, and any suitable combination thereof.

The composition optionally further has a chelating agent. Examples of useful chelating agents include citric acid, isopropyl (mono) citrate, stearyl citrate, lecithin citrate, gluconic acid, tartaric acid, oxalic acid, phosphoric acid, sodium tetrapyrophosphate, potassium monophosphate, sodium hexametaphosphate, calcium hexametaphosphate, sorbitol, glycine (aminoacetic acid), methyl glucamine, triethanolamine (trolamine), EDTA, DEG (dihydroxyethylglycine), DPTA (diethylene triamine pentaacetic acid), NTA (Nitrilotriacetic Acid), HEDTA (N-(hydroxyethyl)-ethylenetriaminetriacetic acid), aminocarboxylates, dimercaperol (BAL), larixinic acid (Maltol), unidentate ligands (fluoride and cyanide ions), diphenylthiocarbazone, 0-phenanthroline, barium diphenylamine sulfonate, sodium glucoheptonate, 8-hydroxyquinoline, olefin complexes (such as dicyclopentadienyl iron), porphyrins, phosphonates, pharmaceutically acceptable salts thereof, derivatives thereof, and any combination thereof.

The composition may further have one or more zinc compounds useful as an astringent. The one or more zinc compounds is selected from the group consisting of water soluble, poorly water soluble and water insoluble zinc salts, compounds and complexes, such as zinc acetate, zinc bacitracin, zinc bromide, zinc caprylate, zinc chloride, zinc citrate, zinc fluoride, zinc formate, zinc glycolate, zinc glycinate, zinc iodate, zinc lactate, zinc nitrate, zinc nitrite, zinc oleate, zinc oxalate, zinc oxide, zinc permanganate, zinc peroxide, zinc phenolsulfonate, zinc phosphate, zinc propionate, zinc pyrophosphate, zinc ricinoleate, zinc salicylate, zinc selenate, zinc silicate, zinc selenide, zinc sulfate, zinc stearate, zinc sulfide, zinc tannate, zinc tartrate, zinc valerate, zinc peptides, and zinc protein complexes. Preferred compounds are zinc lactate and zinc acetate. The one or more zinc compounds is present in an amount about 0.001% to about 30% and more preferably between about 0.1% to about 10%.

In addition to the ingredients enumerated above, the composition optionally may have other ingredients and excipients known in the art as useful in dermatological compositions.

The method of the present invention employs a porous article impregnated with the anti-acne composition to deliver the composition to the skin of a user. The porous article of the delivery system allows for easy application of the composition.

The porous article is preferably made of a material in which the composition is capable of being absorbed and/or adsorbed yet still allowing transmission to the skin to provide suitable contact/bioavailability after application. The porous article can be made from a drapeable or flexible plastic foam, a sponge, a woven or nonwoven natural or synthetic fiber fabric or cloth, including that of gauze, felt, cotton, paper, or any other material capable of absorbing and/or adsorbing the composition. Preferably, the porous article is made of synthetic or natural material and woven or non-woven material. Most preferably, the porous article is made of a non-woven synthetic material(s) in the form of a cloth article. The porous article is flexible and can be easily manipulated by hand.

The porous article can be composed of a single layer or be formed of two or more layers. Different layers can be made of the same or different materials. The porous articles are of discrete size and can be of various forms or shapes, for example, rectangular, circular, or oval. The porous articles can also take the form of a pattern, such as a glove or mitten.

The impregnated porous articles are supplied to the user in the form of a package or container. A plurality of porous articles may be supplied together in a single package or container, or porous articles may be supplied individually packaged. In one embodiment, the porous articles are supplied as individually packaged and hermetically sealed so as to better and more efficiently maintain the moisture content of the articles. The porous articles are also packaged so as to not allow leakage of liquid composition from the container or package. The package or container may be constructed of any material that provides a sufficient barrier to air and/or moisture permeation, such as foil, a plastic-lined foil, or a suitable plastic composition. A plurality of individually packaged impregnated porous articles may be in turn packaged in a larger package or container, such as a box.

If desired, the container may take the form of a plastic, metal, or glass jar suitable for receiving and retaining a plurality of the porous articles. The plastic, metal, or glass jar is made of a suitable plastic, metal, or glass material that does not react with the impregnant composition.

The porous articles are preferably supplied in a moistened state so at to facilitate immediate use by the end user. The article is contacted with an area of the skin affected by acne by touching, dabbing, rubbing, wiping, or similar mechanical motion or action. The contact may be carried out by hand or with by hand in conjunction with a mechanical implement, such as a trowel, brush, or other pad holder that permits a pad surface to contact skin. Contact may be maintained for any period of time but is preferably maintained for a period of time sufficient to effect a desirable degree of cleansing action and deposition of benzoyl peroxide from the article to the skin. Although not deemed to be limiting, the typical user will contact, e.g., rub the article on the surface of the skin for about five seconds or more and more typically about 10 seconds to 30 seconds. When the impregnant composition has a lathering surfactant(s), the user will typically contact the affected area with the article so as to produce a lather simultaneous with the cleansing effect. At the conclusion of contact with the skin, the impregnant composition imparted to the skin, together with any dirt, oils, or lather, are removed by any practical means, such as rinsing off with water or contact with a wet or dry washcloth, towel, or other cloth. Alternately, the impregnant composition may be removed by wiping thoroughly with the composition itself. In that case, the residual benzoyl peroxide may be similar to the originally applied amount. Residual amounts of benzoyl peroxide, an ingredient only sparingly soluble in water, remain on the skin to provide a residual anti-acne effect when the applied amount is removed by rinsing. The amount of residual benzoyl peroxide can be up to about 50 wt % of the applied amount, typically up to 20 wt % and more typically from about 0.1 wt % to about 10 wt % of the benzoyl peroxide originally present in the impregnant composition in the porous article. In other words, the proportion of residual benzoyl peroxide can be considerably less compared to the amount of benzoyl peroxide originally present in the impregnant composition in the porous article but still measurable (and therapeutically and/or prophylactically effective) on the skin.

The method of the present invention can be used to treat existing acne or to facilitate the prevention of acne. Any area of the skin can be treated, although the face and the back are the areas more commonly susceptible to the occurrence of acne.

In an alternate embodiment, the porous articles may be supplied substantially dry, i.e., the water in the impregnant composition (containing the benzoyl peroxide) has been partially or wholly reduced. In this instance, the end user must moisten the porous article with water or other liquid solvent prior to contacting the skin with the article.

The impregnant compositions are stable, i.e., the compositions substantially maintain phase stability and homogeneous dispersion of benzoyl peroxide therewithin at ambient temperature conditions.

The foaming cloth provides efficacious lathering and cleaning of the face. The lather is desirably easily washed of and imparts a cosmetically elegant feel to the skin. After washing, a residual amount of benzoyl peroxide remains on the skin to reduce or diminish the incidence of acne.

The following are examples of the present invention and are not to be construed as limiting.

EXAMPLES

Formulations for impregnant compositions were made. A goal was to provide products with good foaming characteristics and/or good skin application properties and good safety profile. The active formulations are amenable to coating on a non-woven material to make impregnated cloth articles.

Formulations containing benzoyl peroxide as an active ingredient at a concentration of 3%, 6%, and 9% (w/w) were made. Since benzoyl peroxide is practically insoluble in water, the formulations were designed as aqueous gels, wherein the benzoyl peroxide was homogeneously suspended. However, solvents for some or all of the benzoyl peroxide also or alternatively can be used in similar formulations.

Examples 1 to 3

Three formulations were made. The gelling agent used in the formulations was Carbopol 1342. Each of three foaming agents including sodium methyl cocoyl taurate, sodium cocoyl isethionate, and lauramidopropyl betaine were selected since they provided good foaming characteristics. The pH of the formulations was targeted at 5.0-5.5 since it was found to be the most stable and appropriate pH range for benzoyl peroxide topical formulations. The formulation compositions are provided in Table 1.

TABLE 1

(Formulation Compositions of Examples 1 to 3)

| Ingredient | 3% Cleanser % (w/w) | 6% Cleanser % (w/w) | 9% Cleanser % (w/w) |
|---|---|---|---|
| Carbomer 1342, NF | 0.90 | 0.70 | 0.70 |
| Purified Water, USP | 9.918 | 21.539 | 32.301 |
| Docusate Sodium, USP | 0.028 | 0.062 | 0.092 |
| Simethicone Emulsion, USP | 0.007 | 0.015 | 0.023 |
| Benzoyl Peroxide, USP (75%)* | 4.270 | 9.264 | 13.894 |
| Sodium Methyl Cocoyl Taurate | 7.00 | 7.00 | 7.00 |
| Sodium Cocoyl Isethionate | 11.25 | 11.25 | 11.25 |
| Lauramidopropyl Betaine | 6.00 | 6.00 | 6.00 |
| Glycolic Acid, 70% | 0.72 | 0.72 | 0.72 |
| Zinc Lactate | 0.20 | 0.20 | 0.20 |
| Sodium Hydroxide, USP (25%) | qs. pH 5.0 | qs. pH 5.0 | qs. pH 5.0 |
| Purified Water, USP | qs. 100% | qs. 100% | qs. 100% |
| pH | 5.01 | 5.00 | 5.00 |
| Viscosity (T-C @ 5 RPM) | 33,000 cP | 16,300 cP | 27,000 cP |

*BPO was added with 15% overage in 6% and 9% formulations and was added with 6% overage in the 3% formulation. Depending on the circumstances, other overages or no overage may be used.

Example 4

The gelling agent was changed from Carbopol 1342 to Carbopol 940. In addition, 2 thickening agents, methyl gluceth 20 and PEG-150 pentaerythrityl tetrastearate, were added.

TABLE 2

(Formulation Composition of Example 4)
(6% Benzoyl Peroxide)

| | Ingredient | % (w/w) |
|---|---|---|
| A | Purified Water, USP | 32.81 |
|   | Methyl Gluceth 20 | 2.00 |
| B | Purified Water, USP | 5.00 |
|   | Glycolic Acid, 70% | 0.72 |
|   | Zinc Lactate | 0.20 |
| C | Carbomer 940, NF | 0.70 |
| D | Purified Water, USP | 20.00 |
|   | Docusate Sodium, USP | 0.05 |
|   | Simethicone Emulsion, USP | 0.01 |
| E | Benzoyl Peroxide, USP (75%) | 9.26% |
| F | Sodium Methyl Cocoyl Taurate | 7.00 |
|   | PEG-150 Pentaerythrityl Tetrastearate | 0.10 |
|   | Sodium Cocoyl Isethionate | 11.25 |
| G | Lauramidopropyl Betaine | 6.00 |
| H | Sodium Hydroxide, USP (25%) | qs. pH 5.0-5.5 |
| I | Purified Water, USP | qs. 100% |

Examples 5 to 8

Additional formulations were made to enhance physical stability using different combinations of thickening agents. The formulations are set forth in Table 3.

TABLE 3

(Formulations for Examples 5 to 8)

| Formulation | Thickening Agents | Results |
|---|---|---|
| Example 5 | PEG-150 Pentaerythrityl Tetrastearate and Lauramidopropyl Betaine (increased concentrations) | Phase separation occurred even though there were also some process changes by adding zinc lactate and glycolic acid towards the end. |
| Example 6 | PEG-150 Pentaerythrityl Tetrastearate and xanthan gum | Phase separation occurred. |
| Example 7 | Xanthan gum | Phase separation occurred. |
| Example 8 | Hydroxypropyl methylcellulose, Magnesium Aluminum Silicate, cetyl alcohol, and Carbopol | Formulation was fluffy |
| Example 9 | Hydroxypropyl methylcellulose, Veegum, PEG-150 Pentaerythrityl Tetrastearate, and Carbopol | Formulation was fluffy |

Examples 10 to 14

Methyl gluceth 20 in Example 4 was replaced with cetyl alcohol and hydroxypropyl methylcellulose and magnesium aluminum silicate were removed. Additional moisturizers were added. These included 0.1% allantoin, 0.01% sodium hyaluronate, and 0.1% sodium PCA. Lauramidopropyl betaine was replaced with cocamidopropyl betaine.

TABLE 4

(Formulations for Examples 10 to 14)

| | Ingredient | 3% BPO Cleanser Example 10 % (w/w) | 3% BPO Cleanser Example 11 % (w/w) | 6% BPO Cleanser Example 12 % (w/w) | 9% BPO Cleanser Example 13 % (w/w) |
|---|---|---|---|---|---|
| A | Purified Water, USP | 42.86 | 42.76 | 38.40 | 33.83 |
|   | Carbomer 1342, NF | 0.70 | 0.80 | 0.70 | 0.70 |
|   | Hydroxypropyl Methylcellulose | 0.30 | 0.30 | 0.30 | 0.30 |
|   | Allantoin | 0.10 | 0.10 | 0.10 | 0.10 |
|   | Sodium Hyaluronate | 0.01 | 0.01 | 0.01 | 0.01 |

TABLE 4-continued (Formulations for Examples 10 to 14)

| | Ingredient | % (w/w) 3% BPO Cleanser Example 10 | 3% BPO Cleanser Example 11 | 6% BPO Cleanser Example 12 | 9% BPO Cleanser Example 13 |
|---|---|---|---|---|---|
| B | Sodium Methyl Cocoyl Taurate | 7.00 | 7.00 | 7.00 | 7.00 |
| | Sodium Cocoyl Isethionate | 11.25 | 11.25 | 11.25 | 11.25 |
| | Cetyl Alcohol, NF | 1.00 | 1.00 | 1.00 | 1.00 |
| C | Purified Water, USP | 20.00 | 20.00 | 20.00 | 20.00 |
| | Docusate Sodium, USP | 0.05 | 0.05 | 0.05 | 0.05 |
| | Simethicone Emulsion, USP | 0.01 | 0.01 | 0.01 | 0.01 |
| D | Benzoyl Peroxide, USP (75%)* | 4.70 | 4.70 | 9.16 | 13.73 |
| E | Cocamidopropyl Betaine | 6.00 | 6.00 | 6.00 | 6.00 |
| F | Sodium PCA | 0.10 | 0.10 | 0.10 | 0.10 |
| G | Purified Water, USP | 5.00 | 5.00 | 5.00 | 5.00 |
| | Glycolic Acid, 70% | 0.72 | 0.72 | 0.72 | 0.72 |
| | Zinc Lactate | 0.20 | 0.20 | 0.20 | 0.20 |
| H | Sodium Hydroxide, USP (25%) | qs. pH 5.0-5.5 | qs. pH 5.0-5.5 | qs. pH 5.0-5.5 | qs. pH 5.0-5.5 |
| I | Purified Water, USP | qs. 100% | qs. 100% | qs. 100% | qs. 100% |
| | pH | 5.27 | — | 5.23 | 5.23 |
| | Viscosity (T-C @ 5 RPM) | 25,000 cP | 70,000 cP | 60-70,000 cP | 66-79,000 cP |

*These 3% cleansers contained 18% overage. 6% and 9% cleansers contained 15% overage. Other related formulations may contain other overages or no overages depending on circumstances.

The formulation of Example 11 was made with a higher concentration of carbomer (0.8%). The viscosity of this formulation was 70,000 cP.

The formulations were prepared according to the following:
1. In main vessel, mix and heat Phase A to 65-70° C.
2. Continue mixing Phase A until all gums are completely hydrated.
3. At 65-70° C., add Phase B into Phase A and mix until uniform.
4. Begin cooling main batch to 50° C.
5. In a separate vessel, mix and heat Phase C to 65-70° C. Continue mixing until all docusate sodium is dissolved.
6. Cool Phase C to 50° C. and add Phase D.
7. Homogenize combined Phase C with fine screen for 5 minutes.
8. Pass combined Phase C-D through microfluidizer @ 25,000 psi (one pass) directly into main batch under homogenization.
9. Continue homogenization for 10 minutes and switch to propeller mixing with sweep agitation.
10. Add Phase E to main batch and mix until uniform.
11. Add Phase F to main batch and mix until uniform.
12. Premix and warm (30° C.) Phase G until clear. Add to batch and mix until uniform.
13. Adjust pH of batch to 5.0-5.5 with Phase H.
14. qs batch to 100% with purified water (Phase I).

Examples 14 to 17

The formulations were further modified to adjust viscosity according to the following:
1. Removed cocamidopropyl betaine and added 2 levels of glycerin (0.5% and 2%)
2. Removed cocamidopropyl betaine and added 2 levels of glycerin (0.5% and 2%), plus added sodium lauryl sulfoacetate and disodium laureth sulfosuccinate
3. Removed cocamidopropyl betaine and added 2 levels of glycerin (0.5% and 2%), plus added sodium lauryl sulfoacetate and disodium laureth sulfosuccinate and lauramine oxide
4. Removed sodium lauryl sulfoacetate and disodium laureth sulfosuccinate betaine, added 2 levels of glycerin (0.5% and 2%), added lauramine oxide.

Formulations are set forth below in Table 8.

TABLE 8

(Formulations for Examples 14 to 17)

| Example # | Stepan Mild LSB | Glycerin % (w/w) | Viscosity (cP) |
|---|---|---|---|
| Example 14 | Without sodium lauryl, sulfoacetate and disodium laureth sulfosuccinate | 0.5 | 65,000 |
| Example 15 | Without sodium lauryl sulfoacetate and disodium laureth sulfosuccinate | 2.0 | 39,000 |
| Example 16 | With sodium lauryl sulfoacetate and disodium laureth sulfosuccinate | 0.5 | 72,000 |
| Example 17 | With sodium lauryl sulfoacetate and disodium laureth sulfosuccinate | 2.0 | 49,400 |

Formulations having sodium lauryl sulfoacetate and disodium laureth sulfosuccinate had a higher viscosity than formulations without them. Formulations having a higher concentration of glycerin had a lower viscosity than the formulations containing a lower concentration of glycerin.

Examples 18 to 21

The 3% and 6% formulations having adjusted HPMC and Carbopol levels were made. The formulations had two different levels of glycerin (0.5% and 0.1%). The formulations are set forth in Table 9.

TABLE 9

(Formulation Compositions of Examples 18 to 21)

| Phase | Ingredient | 3% BPO Cleanser Example 18 | 3% BPO Cleanser Example 19 | 6% BPO Cleanser Example 20 | 6% BPO Cleanser Example 21 |
|---|---|---|---|---|---|
| A | Purified Water, USP | 42.56 | 42.86 | 38.06 | 38.11 |
|   | Sodium Hyaluronate | 0.01 | 0.01 | 0.01 | 0.01 |
| B | Carbomer 1342, NF | 0.80 | 0.90 | 0.70 | 0.90 |
| C | Hydroxypropyl Methylcellulose (HPMC) | 0.50 | 0.45 | 0.30 | 0.45 |
| D | Allantoin | 0.10 | 0.10 | 0.10 | 0.10 |
|   | Glycerin, USP | 0.50 | 0.10 | 0.50 | 0.10 |
| E | Sodium Methyl Cocoyl Taurate | 7.00 | 7.00 | 7.00 | 7.00 |
|   | Sodium Cocoyl Isethionate | 11.25 | 11.25 | 11.25 | 11.25 |
|   | Cetyl Alcohol, NF | 1.00 | 1.50 | 1.00 | 1.00 |
| F | sodium lauryl sulfoacetate and disodium laureth sulfosuccinate | 4.00 | 4.00 | 4.00 | 4.00 |
| G | Purified Water, USP | 20.00 | 20.00 | 20.00 | 20.00 |
|   | Docusate Sodium, USP | 0.05 | 0.05 | 0.05 | 0.05 |
|   | Simethicone Emulsion, USP | 0.01 | 0.01 | 0.01 | 0.01 |
| H | Benzoyl Peroxide, USP (75%)* | 4.72 | 4.72 | 9.44 | 9.44 |
| I | Sodium PCA | 0.10 | 0.10 | 0.10 | 0.10 |
| J | Purified water, USP | 5.00 | 5.00 | 5.00 | 5.00 |
|   | Glycolic Acid, 70% | 0.72 | 0.72 | 0.72 | 0.72 |
|   | Zinc Lactate | 0.20 | 0.20 | 0.20 | 0.20 |
| K | Sodium Hydroxide, USP (25%) | q.s. pH 5.0-5.5 | q.s. pH 5.0-5.5 | q.s. pH 5.0-5.5 | q.s. pH 5.0-5.5 |
| L | Purified Water, USP | qs. 100% | qs. 100% | qs. 100% | qs. 100% |
|   | Total | 100.00 | 100.00 | 100.00 | 100.00 |

*All formulations contained 18% overage of benzoyl peroxide.

The formulations were prepared according to the following:

1. In main vessel, mix and heat Phase A to 70° C.
2. Continue mixing Phase A until all sodium hyaluronate is completely hydrated.
3. At 70° C., add Phase B into Phase A and mix until all carbomer is hydrated.
4. Add Phase C and mix until all hydroxypropyl methylcellulose is dispersed and hydrated.
5. Maintain 70° C. and add Phase D. Mix until dissolved and uniform.
6. Maintain 70° C. and add Phase E. Mix until completely melted and uniform.
7. Homogenize batch gently being careful not to aerate batch.
8. Add Phase F to batch and mix until uniform.
9. In an appropriately sized vessel, mix and heat Phase G to 55° C. Continue mixing until all Docusate Sodium is dissolved.
10. Cool Phase C to 50° C. and add Phase H.
11. Homogenize combined Phase GH with fine screen for 5 minutes.
12. Cool main batch to 55-60° C. and add Phase GH and mix until uniform using propeller and sweep mixing.
13. **If batch size will allow, homogenize entire batch at this point to make batch uniform. Air must not be incorporated into the batch.
14. Add Phase I and mix until uniform.
15. Premix and warm (30° C.) Phase 3 until clear. Add to batch and mix until uniform.
16. Adjust pH of batch to 5.0-5.5 with Phase K.
17. qs batch to 100% with purified water (Phase L).
18. Mix and cool batch to 20-25° C.

In addition to the modification of the formulations, the methods of making were slightly modified for the formulations of Example 18 and Example 20. Phase GH was added after the batch was cooled to 35-40° C. The temperature was kept in this range with to enhance the chemical stability of benzoyl peroxide in the formulations. At this temperature the batch was thick, so the temperature was changed to 55-60° C. for the formulations of Example 19 and Example 21.

Example 22

A 9% formulation was made. The formulation is set forth in Table 10.

TABLE 10

(Formulation Composition of Example 22)

| Ingredient | % (w/w) 9% Cleanser |
|---|---|
| Sodium Hyaluronate | 0.01 |
| Carbomer 1342, NF | 0.90 |
| Hydroxypropyl Methylcellulose | 0.45 |
| Glycerin, USP | 0.10 |
| Sodium Methyl Cocoyl Taurate | 7.00 |
| Sodium Cocoyl Isethionate | 11.25 |
| Cetyl Alcohol, NF | 1.00 |

TABLE 10-continued (Formulation Composition of Example 22)

| Ingredient | % (w/w) 9% Cleanser |
|---|---|
| sodium lauryl sulfoacetate and disodium laureth sulfosuccinate | 4.00 |
| Docusate Sodium | 0.05 |
| Simethicone Emulsion, USP | 0.01 |
| Benzoyl Peroxide, USP (75%)* | 14.16 |
| Sodium PCA | 0.10 |
| Glycolic Acid, 70% | 0.72 |
| Zinc Lactate | 0.20 |
| Sodium Hydroxide, USP (25%) | q.s. pH 5.0-5.5 |
| Purified Water, USP | q.s. 100% |
| Total | 100.00 |

*The formulation has an 18% overage of benzoyl peroxide.

Example 23

Impregnated porous articles can be prepared using the formulations of the foregoing examples. For instance, impregnated cloth articles can be prepared by exposing a non-woven fabric or cloth to an amount that is suitable to contact the acne-affected area of the skin.

Consumer Use Study (Example 24) and Comparative Examples A and B

A cloth article useful in the method of the present invention and two commercial anti-acne compositions (A and B) were compared in a consumer/user study for efficacy and desirable product features.

A consumer research guidance test was conducted to evaluate the attributes of a facial cleansing cloth (BPO Foaming Cloth) useful in the method of the present invention. The study was conducted at two separate testing facilities. The following Table 11 is a summary of the number of subjects in each age group and gender that completed the study.

TABLE 11

| | | Combined Facilities (n = 193) | Location # 1 (n = 118) | Location # 2 (n = 75) |
|---|---|---|---|---|
| Age Groups | 17 to 22 years old | 141 | 86 | 55 |
| | 23 to 30 years old | 52 | 32 | 20 |
| Gender | Male Subjects | 69 | 52 | 17 |
| | Female Subjects | 124 | 66 | 58 |

There was no attrition from this study at either test location. Subjects 001 through 042 participated in a pilot study at Location # 1.

All subjects were assigned to wash their face with the BPO Foaming Cloth with or without rinsing. Subjects were also assigned to use one of the following commercial facial cleansers (comparative compositions not of the present invention) as determined by a randomization design:
 BPO Cleanser (Benzoyl Peroxide 6%)
 BPO Wash (Benzoyl Peroxide 4%)

The order of test material usage was also determined by the randomization design. All subjects were blinded to all three test materials.

| Test Material Descriptions | |
|---|---|
| (A) Test material identification number (TMIN): | 0357-06CC/0125-07C |
| (B) Test material identification: | BPO Foaming Cloth (Benzoyl Peroxide 6%) |
| (C) Physical description: | White, opaque, medication-coated cloth applicator |
| (D) Test material identification number (TMIN): | 0358-06CC/0162-07C |
| (E) Test material identification: | BPO Cleanser (Benzoyl Peroxide 6%) |
| (F) Physical description: | White, opaque cream |
| (G) Test material identification number (TMIN): | 0359-06CC/0163-07C |
| (H) Test material identification: | BPO Wash (Benzoyl Peroxide 4%) |
| (I) Physical description: | White, opaque cream |

The BPO Cleanser (benzoyl peroxide 6%) used as a comparison composition in the consumer research guidance test had the following ingredients: benzoyl peroxide, glycerin USP, petrolatum USP, C12-15 alkyl benzoate, sodium cocoyl isethionate, special petrolatum fraction, sodium 014-16 olefin sulfonate, zinc lactate, carbomer, potassium metaphosphate NF, titanium dioxide USP, trolamine NF, glycolic acid, lavender extract, and menthol USP.

The BPO Wash (benzoyl peroxide 4%) used as a comparison composition in the consumer research guidance test had the following ingredients: benzoyl peroxide, alpha olefin sulfonate, cetosteryl alcohol NF, glycerin USP, glyceryl monostearate SE, methylparaben NF, phosphoric acid NF, propylene glycol USP, sodium PCA, and whit e soft paraffin USP.

The formulation for the impregnant composition in the BPO Foaming Cloth (Benzoyl Peroxide 6%) used in the consumer research guidance test is set forth below in Table 12.

TABLE 12

(Formulation for BPO Foaming Cloth)

| Phase | CTFA Name | Percent |
|---|---|---|
| A | DEIONIZED WATER | 37.21 |
|   | SODIUM HYALURONATE | 0.01 |
| B | ACRYLATES/C10-30 ALKYL ACRYLATE CROSSPOLYMER | 0.90 |
| C | HYDROXYPROPYL METHYLCELLULOSE | 0.45 |
| D | ALLANTOIN | 0.10 |
|   | GLYCERIN | 0.1 |
| E | SODIUM METHYL COCOYL TAURATE | 7.00 |
|   | SODIUM COCOYL ISOTHIANOATE | 11.25 |
|   | CETYL ALCOHOL | 1.0 |
| F | SODIUM LAURYL SULFOACETATE AND DISODIUM LAURETH SULFOSUCCINATE | 4.00 |
| G | DEIONIZED WATER | 20.00 |
|   | DOCUSATE SODIUM | 0.05 |
|   | SIMETHICONE | 0.01 |
| H | BENZOYL PEROXIDE | 9.44 |
| I | SODIUM PCA | 0.10 |
| J | DEIONIZED WATER | 5.00 |
|   | GLYCOLIC ACID | 0.72 |
|   | ZINC LACTATE | 0.20 |
| K | SODIUM HYDROXIDE 25% | 1.56 |
|   |   | 100.00 |

Subjects were provided with the following usage instructions for each cleanser:

BPO Foaming Cloth:
  Wet the provided facial cleanser cloth with a light stream of tap water.
  Lather and gently wash face with cloth. Do not scrub.
  Rinse thoroughly and pat dry.
BPO Cleanser or BPO Wash
  Lightly wet face and hands with water.
  Dispense an approximately dime-sized amount onto one hand.
  Lather in the hands and apply to the face as you would your normal cleanser.
  Rinse face thoroughly and pat dry.
  Subjects rested quietly in the clinic for at least five minutes prior to washing with the first assigned cleanser (BPO Foaming cloth). At least five minutes after washing with the first cleanser, subjects used the second assigned cleanser (BPO Cleanser or BPO Wash) as instructed.

The first and second washes for subject 054 were separated by two (2) minutes instead of five (5) minutes. This deviation is not expected to have an impact on the outcome of the study.

After completion of washing with the BPO Foaming Cloth, subjects completed a Product Attribute Questionnaire regarding product use. After completion of the final wash, subjects completed a Comparative Questionnaire comparing the BPO Foaming Cloth to the other cleanser (BPO Cleanser or BPO Wash) they were assigned to use.

Questionnaires were tabulated and a top 2 box analysis was performed. Questionnaire analyses were conducted separately for each testing facility, age group, and gender combination. All differences were considered significant at the p 0.05 level.

The tables below present the results of the questionnaire tabulations for both testing facilities combined.

In the Product Attribute Questionnaire, subjects rated their agreement with statements regarding the test material using the following scale:
1=Strongly Agree
2
3=Somewhat Agree
4
5=Strongly Disagree Table 13 presents the results of the top 2 box (positive responses: score of 1 or 2)/bottom 2 box (negative responses: score of 4 or 5) analysis of the questionnaires regarding product attributes. The number of subjects with the specific response is listed, followed by the percentage of the total subject population in parentheses. An asterisk (*) indicates that the proportion of subjects responding positively for a given statement is statistically greater than the proportion of subjects responding negatively.

TABLE 13

(Results of Top 2 Box Analysis for the Product Attribute Questionnaire: BPO Foaming Cloth)

|  |  | All Subjects | | Male Subjects | | Females Subjects | |
| --- | --- | --- | --- | --- | --- | --- | --- |
|  |  | Top 2 box | Bottom 2 Box | Top 2 box | Bottom 2 Box | Top 2 box | Bottom 2 Box |
| 1. Convenient to use | All (17-30 yrs) | *164 (84.9%) | 14 (7.2%) | *55 (79.7%) | 9 (13.0%) | *109 (87.9%) | 5 (4.0%) |
|  | 17-22 yrs old | *122 (86.5%) | 11 (7.8%) | *50 (80.6%) | 8 (12.9%) | *72 (91.1%) | 3 (3.7%) |
|  | 23-30 yrs old | *42 (80.7%) | 3 (5.7%) | 5 (71.4%) | 1 (14.2%) | *37 (82.2%) | 2 (4.4%) |
| 2. Easy to use | All (17-30 yrs) | *166 (86.0%) | 16 (8.2%) | *53 (76.8%) | 8 (11.5%) | *113 (91.1%) | 8 (6.4%) |
|  | 17-22 yrs old | *123 (87.2%) | 9 (6.3%) | *49 (79.0%) | 6 (9.6%) | *74 (93.6%) | 3 (3.7%) |
|  | 23-30 yrs old | *43 (82.6%) | 7 (13.4%) | 4 (57.1%) | 2 (28.5%) | *39 (86.6%) | 5 (11.1%) |
| 3. Portable | All (17-30 yrs) | *178 (92.2%) | 7 (3.6%) | *58 (84.0%) | 5 (7.2%) | *120 (96.7%) | 2 (1.6%) |
|  | 17-22 yrs old | *128 (90.7%) | 5 (3.5%) | *52 (83.8%) | 4 (6.4%) | *76 (96.2%) | 1 (1.2%) |
|  | 23-30 yrs old | *50 (96.1%) | 2 (3.8%) | 6 (85.7%) | 1 (14.2%) | *44 (97.7%) | 1 (2.2%) |
| 4. Easy to use in the shower | All (17-30 yrs) | *155 (80.3%) | 13 (6.7%) | *52 (75.3%) | 7 (10.1%) | *103 (83.0%) | 6 (4.8%) |
|  | 17-22 yrs old | *115 (81.5%) | 8 (5.6%) | *47 (75.8%) | 5 (8.0%) | *68 (86.0%) | 3 (3.7%) |
|  | 23-30 yrs old | *40 (76.9%) | 5 (9.6%) | 5 (71.4%) | 2 (28.5%) | *35 (77.7%) | 3 (6.6%) |
| 5. Easy to use at the sink | All (17-30 yrs) | *168 (87.0%) | 11 (5.6%) | *53 (76.8%) | 7 (10.1%) | *115 (92.7%) | 4 (3.2%) |
|  | 17-22 yrs old | *123 (87.2%) | 8 (5.6%) | *48 (77.4%) | 6 (9.6%) | *75 (94.9%) | 2 (2.5%) |
|  | 23-30 yrs old | *45 (86.5%) | 3 (5.7%) | 5 (71.4%) | 1 (14.2%) | *40 (88.8%) | 2 (4.4%) |
| 6. Amount of lather/foam was appealing | All (17-30 yrs) | *157 (81.3%) | 10 (5.1%) | *46 (66.6%) | 8 (11.5%) | *111 (89.5%) | 2 (1.6%) |
|  | 17-22 yrs old | *114 (80.8%) | 8 (5.6%) | *41 (66.1%) | 7 (11.2%) | *73 (92.4%) | 1 (1.2%) |
|  | 23-30 yrs old | *43 (82.6%) | 2 (3.8%) | 5 (71.4%) | 1 (14.2%) | *38 (84.4%) | 1 (2.2%) |

TABLE 13-continued (Results of Top 2 Box Analysis for the Product Attribute Questionnaire: BPO Foaming Cloth)

| | | | | | | | |
|---|---|---|---|---|---|---|---|
| 7. Provided adequate amount of lather/foam | All (17-30 yrs) | *163 (84.4%) | 11 (5.6%) | *51 (73.9%) | 7 (10.1%) | *112 (90.3%) | 4 (3.2%) |
| | 17-22 yrs old | *118 (83.6%) | 8 (5.6%) | *47 (75.8%) | 6 (9.6%) | *71 (89.8%) | 2 (2.5%) |
| | 23-30 yrs old | *45 (86.5%) | 3 (5.7%) | 4 (57.1%) | 1 (14.2%) | *41 (91.1%) | 2 (4.4%) |
| 8. Provided enough lather to cover face | All (17-30 yrs) | *179 (92.7%) | 6 (3.1%) | *58 (84.0%) | 4 (5.7%) | *121 (97.5%) | 2 (1.6%) |
| | 17-22 yrs old | *129 (91.4%) | 5 (3.5%) | *52 (83.8%) | 4 (6.4%) | *77 (97.4%) | 1 (1.2%) |
| | 23-30 yrs old | *50 (96.1%) | 1 (1.9%) | *6 (85.7%) | 0 (0.0%) | *44 (97.7%) | 1 (2.2%) |
| 9. Provided enough lather to cover chest | All (17-30 yrs) | *123 (63.7%) | 18 (9.3%) | *37 (53.6%) | 10 (14.4%) | *86 (69.3%) | 8 (6.4%) |
| | 17-22 yrs old | *87 (61.7%) | 15 (10.6%) | *33 (53.2%) | 10 (16.1%) | *54 (68.3%) | 5 (6.3%) |
| | 23-30 yrs old | *36 (69.2%) | 3 (5.7%) | 4 (57.1%) | 0 (0.0%) | *32 (71.1%) | 3 (6.6%) |
| 10. Provided enough lather to cover back | All (17-30 yrs) | *90 (46.6%) | 37 (19.1%) | 26 (37.6%) | 16 (23.1%) | *64 (51.6%) | 21 (16.9%) |
| | 17-22 yrs old | *60 (42.5%) | 26 (18.4%) | 23 (37.0%) | 14 (22.5%) | *37 (46.8%) | 12 (15.1%) |
| | 23-30 yrs old | *30 (57.6%) | 11 (21.1%) | 3 (42.8%) | 2 (28.5%) | *27 (60.0%) | 9 (20.0%) |
| 11. Provided adequate amount of lather to cover face, chest, & back | All (17-30 yrs) | 50 (25.9%) | 69 (35.7%) | 16 (23.1%) | 26 (37.6%) | 34 (27.4%) | 43 (34.6%) |
| | 17-22 yrs old | *33 (23.4%) | 56 (39.7%) | 14 (22.5%) | 24 (38.7%) | 19 (24.0%) | 32 (40.5%) |
| | 23-30 yrs old | 17 (32.6%) | 13 (25.0%) | 2 (28.5%) | 2 (28.5%) | 15 (33.3%) | 11 (24.4%) |
| 12. Easily washed off | All (17-30 yrs) | *165 (85.4%) | 10 (5.1%) | *55 (79.7%) | 7 (10.1%) | *110 (88.7%) | 3 (2.4%) |
| | 17-22 yrs old | *122 (86.5%) | 8 (5.6%) | *50 (80.6%) | 6 (9.6%) | *72 (91.1%) | 2 (2.5%) |
| | 23-30 yrs old | *43 (82.6%) | 2 (3.8%) | 5 (71.4%) | 1 (14.2%) | *38 (84.4%) | 1 (2.2%) |
| 13. Left skin feeling smooth | All (17-30 yrs) | *159 (82.3%) | 13 (6.7%) | *55 (79.7%) | 6 (8.6%) | *104 (83.8%) | 7 (5.6%) |
| | 17-22 yrs old | *117 (82.9%) | 10 (7.0%) | *49 (79.0%) | 6 (9.6%) | *68 (86.0%) | 4 (5.0%) |
| | 23-30 yrs old | *42 (80.7%) | 3 (5.7%) | *6 (85.7%) | 0 (0.0%) | *36 (80.0%) | 3 (6.6%) |
| 14. Cosmetically elegant | All (17-30 yrs) | *129 (66.8%) | 17 (8.8%) | *38 (55.0%) | 6 (8.6%) | *91 (73.3%) | 11 (8.8%) |
| | 17-22 yrs old | *92 (65.2%) | 13 (9.2%) | *34 (54.8%) | 5 (8.0%) | *58 (73.4%) | 8 (10.1%) |
| | 23-30 yrs old | *37 (71.1%) | 4 (7.6%) | 4 (57.1%) | 1 (14.2%) | *33 (73.3%) | 3 (6.6%) |
| 15. Left my face feeling clean | All (17-30 yrs) | *175 (90.6%) | 9 (4.6%) | *60 (86.9%) | 6 (8.6%) | *115 (92.7%) | 3 (2.4%) |
| | 17-22 yrs old | *129 (91.4%) | 7 (4.9%) | *55 (88.7%) | 5 (8.0%) | *74 (93.6%) | 2 (2.5%) |
| | 23-30 yrs old | *46 (88.4%) | 2 (3.8%) | 5 (71.4%) | 1 (14.2%) | *41 (91.1%) | 1 (2.2%) |
| 16. Cleansed my face very well | All (17-30 yrs) | *168 (87.0%) | 6 (3.1%) | *58 (84.0%) | 4 (5.7%) | *110 (88.7%) | 2 (1.6%) |
| | 17-22 yrs old | *123 (87.2%) | 5 (3.5%) | *53 (85.4%) | 4 (6.4%) | *70 (88.6%) | 1 (1.2%) |
| | 23-30 yrs old | *45 (86.5%) | 1 (1.9%) | 5 (71.4%) | 0 (0.0%) | *40 (68.8%) | 1 (2.2%) |

| | | | At the Sink | In the Shower | At Sink or in Shower |
|---|---|---|---|---|---|
| 17. When would you use the Cleansing Cloth | All Subjects | All (17-30 yrs) | 64 (33.1%) | 29 (15.0%) | 100 (51.8%) |
| | | 17-22 yrs old | 44 (31.2%) | 22 (15.6%) | 75 (53.1%) |
| | | 23-30 yrs old | 20 (38.4%) | 7 (13.4%) | 25 (48.0%) |
| | Male Subjects | All (17-30 yrs) | 25 (36.2%) | 14 (20.2%) | 30 (43.4%) |
| | | 17-22 yrs old | 22 (35.4%) | 13 (20.9%) | 27 (43.5%) |
| | | 23-30 yrs old | 3 (42.8%) | 1 (14.2%) | 3 (42.8%) |
| | Female Subjects | All (17-30 yrs) | 39 (31.4%) | 15 (12.0%) | 70 (56.4%) |

TABLE 13-continued (Results of Top 2 Box Analysis for the Product Attribute Questionnaire: BPO Foaming Cloth)

| | | | |
|---|---|---|---|
| 17-22 yrs old | 22 (27.8%) | 9 (11.3%) | 48 (60.7%) |
| 23-30 yrs old | 17 (37.7%) | 6 (13.3%) | 22 (48.8%) |

After completion of the final wash, subjects completed a comparative questionnaire regarding the BPO Foaming Cloth and the other cleanser (BPO Cleanser or BPO Wash) which they were assigned to use. Subjects selected which product they preferred for each attribute.

Table 14 presents the results of the top 2 box/bottom 2 box analysis of the questionnaires regarding product preference. The number of subjects with the specific response is listed, followed by the percentage of the total subject population in parentheses. An asterisk (*) indicates that the proportion of subjects who selected BPO Foaming Cloth for a given statement is statistically greater than the proportion of subjects who selected the other assigned cleanser (BPO Cleanser or BPO Wash).

TABLE 14

(Results of Top 2 Box Analysis for the Comparison Questionnaires)

| | | | BPO Foaming Cloths vs. BPO Cleanser (Benzoyl Peroxide 6%) | | BPO Foaming Cloths vs. BPO Wash (Benzoyl Peroxide 4%) | |
|---|---|---|---|---|---|---|
| | | | CLOTH PADS | CLEANSER | CLOTH PADS | CREAMY WASH |
| 1. More convenient to use | All Subjects | All (17-30 yrs) | *78 (80.4%) | 19 (19.5%) | *77 (80.2%) | 19 (19.7%) |
| | | 17-22 yrs old | *58 (81.6%) | 13 (18.3%) | *57 (81.4%) | 13 (18.5%) |
| | | 23-30 yrs old | *20 (76.9%) | 6 (23.0%) | *20 (76.9%) | 6 (23.0%) |
| | Male Subjects | All (17-30 yrs) | *27 (75.0%) | 9 (25.0%) | *24 (72.7%) | 9 (27.2%) |
| | | 17-22 yrs old | *25 (75.7%) | 8 (24.2%) | *22 (75.8%) | 7 (24.1%) |
| | | 23-30 yrs old | 2 (66.6%) | 1 (33.3%) | 2 (50.0%) | 2 (50.0%) |
| | Female Subjects | All (17-30 yrs) | *51 (83.6%) | 10 (16.3%) | *53 (84.1%) | 10 (15.8%) |
| | | 17-22 yrs old | *33 (86.8%) | 5 (13.1%) | *35 (85.3%) | 6 (14.6%) |
| | | 23-30 yrs old | *18 (78.2%) | 5 (21.7%) | *18 (81.8%) | 4 (18.1%) |
| 2. Easier to use | All Subjects | All (17-30 yrs) | *71 (73.1%) | 26 (26.8%) | *69 (71.8%) | 27 (28.1%) |
| | | 17-22 yrs old | *52 (73.2%) | 19 (26.7%) | *52 (74.2%) | 18 (25.7%) |
| | | 23-30 yrs old | *19 (73.0%) | 7 (26.9%) | 17 (65.3%) | 9 (34.6%) |
| | Male Subjects | All (17-30 yrs) | 24 (66.6%) | 12 (33.3%) | 22 (66.6%) | 11 (33.3%) |
| | | 17-22 yrs old | 22 (66.6%) | 11 (33.3%) | 20 (68.9%) | 9 (31.0%) |
| | | 23-30 yrs old | 2 (66.6%) | 1 (33.3%) | 2 (50.0%) | 2 (50.0%) |
| | Female Subjects | All (17-30 yrs) | *47 (77.0%) | 14 (22.9%) | *47 (74.6%) | 16 (25.3%) |
| | | 17-22 yrs old | *30 (78.9%) | 8 (21.0%) | *32 (78.0%) | 9 (21.9%) |
| | | 23-30 yrs old | *17 (73.9%) | 6 (26.0%) | 15 (68.1%) | 7 (31.8%) |
| 3. More portable | All Subjects | All (17-30 yrs) | *95 (97.9%) | 2 (2.0%) | *91 (94.7%) | 5 (5.2%) |
| | | 17-22 yrs old | *69 (97.1%) | 2 (2.8%) | *67 (95.7%) | 3 (4.2%) |
| | | 23-30 yrs old | *26 (100.0%) | 0 (0.0%) | *24 (92.3%) | 2 (7.6%) |
| | Male Subjects | All (17-30 yrs) | *36 (100.0%) | 0 (0.0%) | *30 (90.9%) | 3 (9.0%) |
| | | 17-22 yrs old | *33 (100.0%) | 0 (0.0%) | *28 (96.5%) | 1 (3.4%) |
| | | 23-30 yrs old | 3 (100.0%) | 0 (0.0%) | 2 (50.0%) | 2 (50.0%) |
| | Female Subjects | All (17-30 yrs) | *59 (96.7%) | 2 (3.2%) | *61 (96.8%) | 2 (3.1%) |
| | | 17-22 yrs | *36 | 2 | *39 | 2 |

TABLE 14-continued (Results of Top 2 Box Analysis for the Comparison Questionnaires)

|  |  |  | BPO Foaming Cloths vs. BPO Cleanser (Benzoyl Peroxide 6%) | | BPO Foaming Cloths vs. BPO Wash (Benzoyl Peroxide 4%) | |
|---|---|---|---|---|---|---|
|  |  |  | CLOTH PADS | CLEANSER | CLOTH PADS | CREAMY WASH |
|  |  | old | (94.7%) | (5.2%) | (95.1%) | (4.8%) |
|  |  | 23-30 yrs old | *23 (100.0%) | 0 (0.0%) | *22 (100.0%) | 0 (0.0%) |
| 4. Lather/foam was more appealing | All Subjects | All (17-30 yrs) | *81 (83.5%) | 16 (16.4%) | *77 (80.2%) | 19 (19.7%) |
|  |  | 17-22 yrs old | *59 (83.0%) | 12 (16.9%) | *56 (80.0%) | 14 (20.0%) |
|  |  | 23-30 yrs old | *22 (84.6%) | 4 (15.3%) | *21 (80.7%) | 5 (19.2%) |
|  | Male Subjects | All (17-30 yrs) | *30 (83.3%) | 6 (16.6%) | *25 (75.7%) | 8 (24.2%) |
|  |  | 17-22 yrs old | *28 (84.8%) | 5 (15.1%) | *23 (79.3%) | 6 (20.6%) |
|  |  | 23-30 yrs old | 2 (66.6%) | 1 (33.3%) | 2 (50.0%) | 2 (50.0%) |
|  | Female Subjects | All (17-30 yrs) | *51 (83.6%) | 10 (16.3%) | *52 (82.5%) | 11 (17.4%) |
|  |  | 17-22 yrs old | *31 (81.5%) | 7 (18.4%) | *33 (80.4%) | 8 (19.5%) |
|  |  | 23-30 yrs old | *20 (86.9%) | 3 (13.0%) | *19 (86.3%) | 3 (13.6%) |
| 5. Provides a more adequate amount of lather foam | All Subjects | All (17-30 yrs) | *85 (87.6%) | 12 (12.3%) | *72 (75.0%) | 24 (25.0%) |
|  |  | 17-22 yrs old | *62 (87.3%) | 9 (12.6%) | *53 (75.7%) | 17 (24.2%) |
|  |  | 23-30 yrs old | *23 (88.4%) | 3 (11.5%) | *19 (73.0%) | 7 (26.9%) |
|  | Male Subjects | All (17-30 yrs) | *30 (83.3%) | 6 (16.6%) | 19 (57.5%) | 14 (42.4%) |
|  |  | 17-22 yrs old | *28 (84.8%) | 5 (15.1%) | 18 (62.0%) | 11 (37.9%) |
|  |  | 23-30 yrs old | 2 (66.6%) | 1 (33.3%) | 1 (25.0%) | 3 (75.0%) |
|  | Female Subjects | All (17-30 yrs) | *55 (90.1%) | 6 (9.8%) | *53 (84.1%) | 10 (15.8%) |
|  |  | 17-22 yrs old | *34 (89.4%) | 4 (10.5%) | *35 (85.3%) | 6 (14.6%) |
|  |  | 23-30 yrs old | *21 (91.3%) | 2 (8.6%) | *18 (81.8%) | 4 (18.1%) |
| 6. Produced more lather to cover face | All Subjects | All (17-30 yrs) | *84 (86.5%) | 13 (13.4%) | *71 (73.9%) | 25 (26.0%) |
|  |  | 17-22 yrs old | *62 (87.3%) | 9 (12.6%) | *50 (71.4%) | 20 (28.5%) |
|  |  | 23-30 yrs old | *22 (84.6%) | 4 (15.3%) | *21 (80.7%) | 5 (19.2%) |
|  | Male Subjects | All (17-30 yrs) | *31 (86.1%) | 5 (13.8%) | 20 (60.6%) | 13 (39.3%) |
|  |  | 17-22 yrs old | *28 (84.8%) | 5 (15.1%) | 17 (58.6%) | 12 (41.3%) |
|  |  | 23-30 yrs old | 3 (100.0%) | 0 (0.0%) | 3 (75.0%) | 1 (25.0%) |
|  | Female Subjects | All (17-30 yrs) | *53 (86.8%) | 8 (13.1%) | *51 (80.9%) | 12 (19.0%) |
|  |  | 17-22 yrs old | *34 (89.4%) | 4 (10.5%) | *33 (80.4%) | 8 (19.5%) |
|  |  | 23-30 yrs old | *19 (82.6%) | 4 (17.3%) | *18 (81.8%) | 4 (18.1%) |
| 7. Produced more lather to cover chest | All Subjects | All (17-30 yrs) | *79 (81.4%) | 18 (18.5%) | *61 (63.5%) | 35 (36.4%) |
|  |  | 17-22 yrs old | *57 (80.2%) | 14 (19.7%) | 41 (58.5%) | 29 (41.4%) |
|  |  | 23-30 yrs old | *22 (84.6%) | 4 (15.3%) | *20 (76.9%) | 6 (23.0%) |
|  | Male Subjects | All (17-30 yrs) | *28 (77.7%) | 8 (22.2%) | 16 (48.4%) | 17 (51.5%) |
|  |  | 17-22 yrs old | *25 (75.7%) | 8 (24.2%) | 14 (48.2%) | 15 (51.7%) |
|  |  | 23-30 yrs old | 3 (100.0%) | 0 (0.0%) | 2 (50.0%) | 2 (50.0%) |
|  | Female Subjects | All (17-30 yrs) | *51 (83.6%) | 10 (16.3%) | *45 (71.4%) | 18 (28.5%) |
|  |  | 17-22 yrs | *32 | 6 | 27 | 14 |

TABLE 14-continued (Results of Top 2 Box Analysis for the Comparison Questionnaires)

| | | | BPO Foaming Cloths vs. BPO Cleanser (Benzoyl Peroxide 6%) | | BPO Foaming Cloths vs. BPO Wash (Benzoyl Peroxide 4%) | |
|---|---|---|---|---|---|---|
| | | | CLOTH PADS | CLEANSER | CLOTH PADS | CREAMY WASH |
| | | old | (84.2%) | (15.7%) | (65.8%) | (34.1%) |
| | | 23-30 yrs old | *19 (82.6%) | 4 (17.3%) | *18 (81.8%) | 4 (18.1%) |
| 8. Produced more lather to cover back | All Subjects | All (17-30 yrs) | *79 (81.4%) | 18 (18.5%) | *60 (62.5%) | 36 (37.5%) |
| | | 17-22 yrs old | *58 (81.6%) | 13 (18.3%) | 40 (57.1%) | 30 (42.8%) |
| | | 23-30 yrs old | *21 (80.7%) | 5 (19.2%) | *20 (76.9%) | 6 (23.0%) |
| | Male Subjects | All (17-30 yrs) | *29 (80.5%) | 7 (19.4%) | 16 (48.4%) | 17 (51.5%) |
| | | 17-22 yrs old | *26 (78.7%) | 7 (21.2%) | 14 (48.2%) | 15 (51.7%) |
| | | 23-30 yrs old | 3 (100.0%) | 0 (0.0%) | 2 (50.0%) | 2 (50.0%) |
| | Female Subjects | All (17-30 yrs) | *50 (81.9%) | 11 (18.0%) | *44 (69.8%) | 19 (30.1%) |
| | | 17-22 yrs old | *32 (84.2%) | 6 (15.7%) | 26 (63.4%) | 15 (36.5%) |
| | | 23-30 yrs old | *18 (78.2%) | 5 (21.7%) | *18 (81.8%) | 4 (18.1%) |
| 9. Produced more lather to cover face, chest, back and trunk | All Subjects | All (17-30 yrs) | *78 (80.4%) | 19 (19.5%) | 57 (59.3%) | 39 (40.6%) |
| | | 17-22 yrs old | *56 (78.8%) | 15 (21.1%) | 38 (54.2%) | 32 (45.7%) |
| | | 23-30 yrs old | *22 (84.6%) | 4 (15.3%) | *19 (73.0%) | 7 (26.9%) |
| | Male Subjects | All (17-30 yrs) | *27 (75.0%) | 9 (25.0%) | 17 (51.5%) | 16 (48.4%) |
| | | 17-22 yrs old | *24 (72.7%) | 9 (27.2%) | 15 (51.7%) | 14 (48.2%) |
| | | 23-30 yrs old | 3 (100.0%) | 0 (0.0%) | 2 (50.0%) | 2 (50.0%) |
| | Female Subjects | All (17-30 yrs) | *51 (83.6%) | 10 (16.3%) | *40 (63.4%) | 23 (36.5%) |
| | | 17-22 yrs old | *32 (84.2%) | 6 (15.7%) | 23 (56.0%) | 13 (43.9%) |
| | | 23-30 yrs old | *19 (82.6%) | 4 (17.3%) | *17 (77.2%) | 5 (22.7%) |
| 10. More Cosmetically Elegant | All Subjects | All (17-30 yrs) | *73 (75.2%) | 24 (24.7%) | *74 (77.0%) | 22 (22.9%) |
| | | 17-22 yrs old | *54 (76.0%) | 17 (23.9%) | *55 (78.5%) | 15 (21.4%) |
| | | 23-30 yrs old | *19 (73.0%) | 7 (26.9%) | *19 (73.0%) | 7 (26.9%) |
| | Male Subjects | All (17-30 yrs) | *25 (69.4%) | 11 (30.5%) | *27 (81.8%) | 6 (18.1%) |
| | | 17-22 yrs old | *23 (69.6%) | 10 (30.3%) | *25 (86.2%) | 4 (13.7%) |
| | | 23-30 yrs old | 2 (66.6%) | 1 (33.3%) | 2 (50.0%) | 2 (50.0%) |
| | Female Subjects | All (17-30 yrs) | *48 (78.6%) | 13 (21.3%) | *47 (74.6%) | 16 (25.3%) |
| | | 17-22 yrs old | *31 (81.5%) | 7 (18.4%) | *30 (73.1%) | 11 (26.8%) |
| | | 23-30 yrs old | *17 (73.9%) | 6 (26.0%) | *17 (77.2%) | 5 (22.7%) |
| 11. Which product do you prefer | All Subjects | All (17-30 yrs) | *75 (77.3%) | 22 (22.6%) | *75 (78.1%) | 21 (21.8%) |
| | | 17-22 yrs old | *56 (78.8%) | 15 (21.1%) | *56 (80.0%) | 14 (20.0%) |
| | | 23-30 yrs old | *19 (73.0%) | 7 (26.9%) | *19 (73.0%) | 7 (26.9%) |
| | Male Subjects | All (17-30 yrs) | *28 (77.7%) | 8 (22.2%) | 22 (66.6%) | 11 (33.3%) |
| | | 17-22 yrs old | *26 (78.7%) | 7 (21.2%) | 20 (68.9%) | 9 (31.0%) |
| | | 23-30 yrs old | 2 (66.6%) | 1 (33.3%) | 2 (50.0%) | 2 (50.0%) |

TABLE 14-continued (Results of Top 2 Box Analysis for the Comparison Questionnaires)

| | | BPO Foaming Cloths vs. BPO Cleanser (Benzoyl Peroxide 6%) | | BPO Foaming Cloths vs. BPO Wash (Benzoyl Peroxide 4%) | |
|---|---|---|---|---|---|
| | | CLOTH PADS | CLEANSER | CLOTH PADS | CREAMY WASH |
| Female Subjects | All (17-30 yrs) | *47 (77.0%) | 14 (22.9%) | *53 (84.1%) | 10 (15.8%) |
| | 17-22 yrs old | *30 (78.9%) | 8 (21.0%) | *36 (87.8%) | 5 (12.1%) |
| | 23-30 yrs old | *17 (73.9%) | 6 (26.0%) | *17 (77.2%) | 5 (22.7%) |

The following Table 15 summarizes the results of the top 2 box/bottom 2 box analysis for the Product Attribute Questionnaire. An asterisk (*) indicates that a statistically significant proportion of subjects responded positively (Strongly Agree/Agree—score of 1 or 2) than negatively (Disagree/Strongly Disagree—score of 4 or 5).

TABLE 15

(Summary of Results for the Product Attribute Questionnaire - The Monadic Ratings of the BPO Foaming Cloth)

| | All Subjects | | | Male Subjects | | | Female Subjects | | |
|---|---|---|---|---|---|---|---|---|---|
| | All (17-30 yrs) | 17-22 yrs old | 23-30 yrs old | All (17-30 yrs) | 17-22 yrs old | 23-30 yrs old | All (17-30 yrs) | 17-22 yrs old | 23-30 yrs old |
| 1. Convenient to use | * | * | * | * | * | | * | * | * |
| 2. Easy to use | * | * | * | * | * | | * | * | * |
| 3. Portable | * | * | * | * | * | | * | * | * |
| 4. Easy to use in the shower | * | * | * | * | * | | * | * | * |
| 5. Easy to use at the sink | * | * | * | * | * | | * | * | * |
| 6. Amount of lather was appealing | * | * | * | * | * | | * | * | * |
| 7. Provided adequate amount of foam | * | * | * | * | * | | * | * | * |
| 8. Provided enough lather to cover face | * | * | * | * | * | * | * | * | * |
| 9. Provided enough lather to cover chest | * | * | * | * | * | | * | * | * |
| 10. Provided enough lather to cover back | * | * | * | | | | * | * | * |
| 11. Provided lather to cover face/chest/back | | * | | | | | | | |
| 12. Easily washed off | * | * | * | * | * | | * | * | * |
| 13. Left skin feeling smooth | * | * | * | * | * | | * | * | * |
| 14. Cosmetically elegant | * | * | * | * | * | | * | * | * |
| 15. Left my face feeling clean | * | * | * | * | * | | * | * | * |
| 16. Cleansed my face very well | * | * | * | * | * | | * | * | * |

The following Tables 16 and 17 summarize the results of the top 2 box/bottom 2 box analysis for the Comparative Questionnaire. An asterisk (*) indicates that a statistically significant proportion of subjects selected BPO Foaming Cloth for a given statement than the other assigned cleanser (BPO Cleanser or BPO Wash).

TABLE 16

(Summary of Results for the Comparative Questionnaire
for the BPO Foaming Cloth vs. the BPO Cleanser)

|  | BPO Foaming Cloth vs. BPO Cleanser (Benzoyl Peroxide 6%) | | | | | | | | |
|---|---|---|---|---|---|---|---|---|---|
|  | All Subjects | | | Male Subjects | | | Female Subjects | | |
|  | All (17-30 yrs) | 17-22 yrs old | 23-30 yrs old | All (17-30 yrs) | 17-22 yrs old | 23-30 yrs old | All (17-30 yrs) | 17-22 yrs old | 23-30 yrs old |
| 1. More convenient to use | * | * | * | * | * |  | * | * | * |
| 2. Easier to use | * | * | * |  |  |  | * | * | * |
| 3. More portable | * | * | * | * | * |  | * | * | * |
| 4. Lather/foam was more appealing | * | * | * | * | * |  | * | * | * |
| 5. Provides more adequate amount of lather | * | * | * | * | * |  | * | * | * |
| 6. Produced more lather to cover face | * | * | * | * | * |  | * | * | * |
| 7. Produced more lather to cover chest | * | * | * | * | * |  | * | * | * |
| 8. Produced more lather to cover back | * | * | * | * | * |  | * | * | * |
| 9. Produced more lather to cover face/chest/back/trunk | * | * | * | * | * |  | * | * | * |
| 10. More Cosmetically Elegant | * | * | * | * | * |  | * | * | * |
| 11. Which product do you prefer | * | * | * | * | * |  | * | * | * |

TABLE 17

(Summary of Results for the Comparative Questionnaire
for the BPO Foaming Cloth vs. the BPO Wash)

|  | BPO Foaming Cloth vs. BPO Wash (Benzoyl Peroxide 4%) | | | | | | | | |
|---|---|---|---|---|---|---|---|---|---|
|  | All Subjects | | | Male Subjects | | | Female Subjects | | |
|  | All (17-30 yrs) | 17-22 yrs old | 23-30 yrs old | All (17-30 yrs) | 17-22 yrs old | 23-30 yrs old | All (17-30 yrs) | 17-22 yrs old | 23-30 yrs old |
| 1. More convenient to use | * | * | * | * | * |  | * | * | * |
| 2. Easier to use | * | * |  |  |  |  | * | * |  |
| 3. More portable | * | * | * | * | * |  | * | * | * |
| 4. Lather/foam was more appealing | * | * | * | * | * |  | * | * | * |
| 5. Provides more adequate amount of lather | * | * | * |  |  |  | * | * | * |
| 6. Produced more lather to cover face | * | * | * |  |  |  | * | * | * |
| 7. Produced more lather to cover chest | * |  | * |  |  |  | * |  | * |
| 6. Produced more lather to cover back | * |  | * |  |  |  | * |  | * |
| 9. Produced more lather to cover face/chest/back/trunk |  |  | * |  |  |  | * |  | * |
| 10. More Cosmetically Elegant | * | * | * | * | * |  | * | * | * |
| 11. Which product do you prefer | * | * | * |  |  |  | * | * | * |

Overall, the results from the Product Attribute Questionnaire (only used for BPO Foaming Cloth) were very positive with statistically significant top wins for all questions. Moreover, the results from the Comparative Questionnaires showed significant wins for the BPO Foaming Cloth compared to BPO Cleanser and BPO Wash for questions 1-4 (related to convenience of use and aesthetic properties), and questions 5-9 (related to product coverage). Questions 10 and 11 showed significant wins for BPO Foaming Cloth Pads (Question 10: "More Cosmetically Elegant" and Question 11: "Product Preference").

Similar results were obtained when hard water was used as the test medium. The maximum foam height generated by BPO Foaming Cloths was 6.1±0.3 cm. The residual foam height after 5 minutes remained high at 4.5±0.3 cm for BPO Foaming Cloths. Comparing to other cleansing products, the maximum foam height generated by BPO Foaming Cloths was 3 and 2 times of that by BPO Cleanser and BPO Wash, respectively. The residual foam height after 5 minutes for BPO Foaming Cloths was 6 and 3 times of that for BPO Cleanser and BPO Wash, respectively. The results are set forth below in Table 18.

TABLE 18

| | | (Blender Foam Volume Test Results) | | | | | |
|---|---|---|---|---|---|---|---|
| Testing | | BPO Foaming Cloths | | BPO Cleanser 6% | | BPO Wash 4% | |
| Medium | Test Parameters | Average | STDEV | Average | STDEV | Average | STDEV |
| DI Water | Fm (maximum foam height) (cm) | 7.4 | 0.3 | 1.8 | 0.1 | 2.8 | 0.1 |
| | Fr (residual foam after 5 min) (cm) | 5.6 | 0.3 | 0.3 | 0.2 | 1.4 | 0.3 |
| Hard Water (100 ppm) | Fm (maximum foam height) (cm) | 6.1 | 0.3 | 1.9 | 0.2 | 3.1 | 0.3 |
| | Fr (residual foam after 5 min) (cm) | 4.5 | 0.3 | 0.7 | 0.2 | 1.6 | 0.1 |

The BPO Foaming Cloth may provide a higher degree of lathering compared to the BPO Cleanser and the BPO Wash. Further, the BPO Foaming Cloth may impart a higher degree of cosmetically elegant feel to the skin compared to the BPO Cleanser and the BPO Wash. Further, the BPO Foaming Cloth may leave a higher degree of a residual benzoyl peroxide on the skin compared to the BPO Cleanser and the BPO Wash after wash-off.

Foaming Tendency

The foaming tendency of the BPO Foaming Cloth was also tested and compared to that of the BPO Cleanser and the BPO Wash.

The test method employed was ASTM D-3519-88. The test method was used to measure foaming tendency in aqueous media under high shear conditions (blender test). The testing was performed with deionized (DI) water and hard water (100 ppm) in triplicate. The test samples were prepared by cutting two pads of BPO Foaming Cloths into small pieces and adding them to 190 mL of water. The test samples for BPO Cleanser and BPO Wash were prepared by adding 10 mL of the test product into 190 mL of water. The test samples were equilibrated for 1 hour in a 25±1° C. water bath. The foam volume was determined after blending for 30 seconds using a blender with a glass jar agitating between 8000 and 9000 rpm. The residual foam height was also determined after allowing the blender to stand undisturbed for 5 minutes.

Data Summary

The testing results of maximum foam height and residual foam height after 5 min are summarized in Table 18. When DI water was used as the test medium, the maximum foam height generated by BPO Foaming Cloths was 7.4±0.3 cm. The residual foam height after 5 minutes remained high at 5.6±0.3 cm for BPO Foaming Cloths. Comparing to other cleansing products, the maximum foam height generated by BPO Cloths was 4 and 3 times of that by BPO Cleanser and BPO Wash, respectively. The residual foam height after 5 minutes for BPO Foaming Cloths was 19 and 4 times of that for BPO Cleanser and BPO Wash, respectively.

It should be understood that the foregoing description is only illustrative of the present invention. Various alternatives and modifications can be devised by those skilled in the art without departing from the invention. Accordingly, the present invention is intended to embrace all such alternatives, modifications and variances which fall within the scope of the appended claims.

What is claimed is:

1. An article for use in the treatment of acne, comprising
   A fabric or cloth pad,
   A liquid composition impregnated on the pad, comprising benzoyl peroxide, and one or more surfactants, wherein the surfactants are present in sufficient quantity to make the composition foamable, and wherein the surfactants comprise 4% to 40% by weight of the composition, and the composition has a viscosity of 30,000 cP to 150,000 cP.

2. The article of claim 1 wherein the surfactants comprise 10% to 30% by weight of the composition.

3. The article of claim 1 wherein the surfactants comprise 23.25% to 24.25 % by weight of the composition.

4. The article of claim 1 wherein the viscosity is 35,000 cP to 65,000 cP.

5. An article for use in the treatment of acne, comprising
   A fabric or cloth pad.
   A liquid composition impregnated on the pad, comprising benzoyl peroxide, and one or more surfactants, wherein the surfactants are present in sufficient quantity to make the composition foamable, and wherein the surfactants comprise 4% to 40% by weight of the composition, and the composition has a viscosity of at least 30,000 cP.

6. The article of claim 5 wherein the viscosity is at least 35,000 cP.

7. The article of claim 5 wherein the viscosity is 35,000 cP to 65,000 cP.

8. The article of claim 5 wherein the viscosity is 30,000 cP to 150,000 cP.

9. The article of claim 5 wherein the surfactants comprise 10% to 30% by weight of the composition.

10. The article of claim 5 wherein the surfactants comprise 23.25% to 24.25% by weight of the composition.

11. The article of claim 1 wherein the liquid composition further comprises 10% to 90% water by total weight of the liquid composition.

12. The article of claim 5 wherein the liquid composition further comprises 10% to 90% water by total weight of the liquid composition.

* * * * *

UNITED STATES PATENT AND TRADEMARK OFFICE
CERTIFICATE OF CORRECTION

| | | |
|---|---|---|
| PATENT NO. | : 8,263,097 B2 | Page 1 of 1 |
| APPLICATION NO. | : 13/335151 | |
| DATED | : September 11, 2012 | |
| INVENTOR(S) | : Waranush Jitpraphai et al. | |

It is certified that error appears in the above-identified patent and that said Letters Patent is hereby corrected as shown below:

In Column 29, Table 17, replace "6. Produced more lather to cover back" with --8. Produced more lather to cover back--.

Signed and Sealed this
Twenty-seventh Day of November, 2012

David J. Kappos
*Director of the United States Patent and Trademark Office*